United States Patent
Asakura

(10) Patent No.: US 8,348,974 B2
(45) Date of Patent: Jan. 8, 2013

(54) SPINNING SOLUTION COMPOSITION, PROCESS FOR PRODUCING REGENERATED SILK FIBER USING THE COMPOSITION, AND REGENERATED SILK FIBER PRODUCED BY THE PROCESS

(75) Inventor: Tetsuo Asakura, Fuchu (JP)

(73) Assignee: National University Corporation Tokyo University of Agriculture and Technology, Fuchu-shi (JP)

( * ) Notice: Subject to any disclaimer, the term of this patent is extended or adjusted under 35 U.S.C. 154(b) by 706 days.

(21) Appl. No.: 12/307,208

(22) PCT Filed: Mar. 1, 2007

(86) PCT No.: PCT/JP2007/053929
§ 371 (c)(1),
(2), (4) Date: Jan. 12, 2009

(87) PCT Pub. No.: WO2008/004356
PCT Pub. Date: Jan. 10, 2008

(65) Prior Publication Data
US 2009/0318963 A1 Dec. 24, 2009

(30) Foreign Application Priority Data
Jul. 4, 2006 (JP) ................................. 2006-184483

(51) Int. Cl.
*A61B 17/04* (2006.01)
*A61L 17/00* (2006.01)
*C09K 3/00* (2006.01)
*A61K 47/00* (2006.01)
*D01F 4/00* (2006.01)

(52) U.S. Cl. .................... 606/231; 252/182.12; 514/773; 264/202

(58) Field of Classification Search .................. 424/490; 606/231; 514/773; 264/202; 252/182.12
See application file for complete search history.

(56) References Cited

U.S. PATENT DOCUMENTS
5,252,285 A * 10/1993 Lock .............................. 264/202
2003/0183978 A1 10/2003 Asakura
2004/0185737 A1 9/2004 Asakura
2005/0055051 A1* 3/2005 Grafton ......................... 606/228

FOREIGN PATENT DOCUMENTS
JP 4 194063 7/1992
JP 2000 170029 6/2000
(Continued)

OTHER PUBLICATIONS
Kosuke Ohgo et al. ("Application of silk fibroins and Silk-like Proteins as Material for Regenerative Medicine," in Polymer Preprints, vol. 55, No. 1, May 25, 2006, provided by applicant on Form 1449).*

(Continued)

*Primary Examiner* — Blessing Fubara
(74) *Attorney, Agent, or Firm* — Oblon, Spivak, McClelland, Maier & Neustadt, L.L.P.

(57) ABSTRACT

A spinning solution composition which provides regenerated silk fiber that exhibits a strength and elongation close to those of natural silk fiber, is rapidly degradable in vivo, and can be caused to have ability to gradually release a drug to prevent inflammation; a process for producing such regenerated silk fiber by use of the composition; and regenerated silk fiber obtained through the process.

5 Claims, 3 Drawing Sheets

FOREIGN PATENT DOCUMENTS

| | | |
|---|---|---|
| JP | 2001 98450 | 4/2001 |
| JP | 2004 68161 | 3/2004 |
| WO | 93 15244 | 8/1993 |

OTHER PUBLICATIONS

Ohgo et al. ("Accumulation of Basic Findings toward Application of Silk Fibroins as Material for Regenerative Medicine," in Fiber Preprints, vol. 61, No. 2 (Symposia) Jun. 14 2006, provided by applicant on Form 1449).*

O Kosuke Ohgo, et al., "Application of Silk Fibroins and Silk-Like Proteins as Material for Regenerative Medicine", Polymer Preprints, vol. 55, No. 1, May 25, 2006, 6 pages (with English Abstract and English translation).

O Kosuke Ohgo, et al., "Accumulation of Basic Findings Toward Application of Silk Fibroins as Material for Regenerative Medicine", Fiber Preprints, vol. 61, No. 2 (Symposia), Jun. 14, 2006, 8 pages (with English translation).

Noda, Hiroyuki "Introduction of Development research of high-value-added silk product obtained by a functional dyeing", Intitute for Life Support Technologhy, Yamagata Public Corporation for the Development of Industry, No. 6, pp. 6-7, 2001, (with partial English translation).

* cited by examiner

A                                    B

| sample | time | Day 1 | Day 9 |
|---|---|---|---|
| Drawn (3-times) | enzym |  |  |
| | PBS |  |  |
| Natural fiber | enzym |  |  |
| | PBS |  |  |

SPINNING SOLUTION COMPOSITION, PROCESS FOR PRODUCING REGENERATED SILK FIBER USING THE COMPOSITION, AND REGENERATED SILK FIBER PRODUCED BY THE PROCESS

CROSS-REFERENCE TO RELATED APPLICATIONS

This application is a 371 of PCT/JP2007/053929 filed Mar. 1, 2007 and claims the benefit of JP 2006-184483 filed Jul. 4, 2006.

TECHNICAL FIELD

The present invention relates to a spinning solution composition, to a process for producing regenerated silk fiber using the composition, and to regenerated silk fiber produced by the process. More particularly, the present invention relates to a spinning solution composition suitable for producing regenerated silk fiber that exhibits strength and elongation approximating those of natural silk fiber, that quickly degrades in vivo, and that also can prevent inflammation by gradually releasing a drug, to a process for producing such regenerated silk fiber using the composition, and to regenerated silk fiber produced by the process.

BACKGROUND ART

Silk fiber is a natural fiber having high biocompatibility. It is thin, strong, and has appropriate elasticity and softness. In addition, it exhibits a remarkable sliding property when spun into thread, and is easily manageable both in tying and untying. Therefore, silk fiber is often used as a surgical suture. Because silk is a protein in nature, silk suture is gradually decomposed and can be absorbed by the body even when stitches are left in the body. However, since the rate of degradation in vivo is slow, silk suture is usually categorized as a non-absorbable suture material, which is to be removed from the body. There are other types of sutures, such as regenerated collagen, which are degraded and absorbed in vivo, and stitches produced thereby do not have to be removed. However, since this type of suture has strength only one tenth that of silk suture, its resiliency is low and knot tying is not easy.

Production of regenerated silk thread from silk fiber of domesticated silkworms (hereinafter may be referred to simply as "domesticated silkworm silk fiber") typically involves use of a solvent for dissolving silk fibroin originating from domesticated silkworms (hereinafter this fibroin may be referred to simply as "domesticated silkworm silk fibroin"), including an aqueous solution of a neutral salt (such as lithium bromide) or an aqueous solution of a complex salt (such as copper ethylenediamine). Since these aqueous solutions act to rupture strong hydrogen bonds in the β-sheet structure of silk fibroin, the following problems have been noted. That is, if the silk fibroin is left in the solvent over a long period of time, even molecular chains are ruptured thereby decreasing the molecular weight; salts tend to remain; and the resultant regenerated silk fiber exhibits poor mechanical properties.

Incidentally, hexafluoroisopropanol (HFIP) has been known as a solvent which prevents a decrease in molecular weight of silk fibroin and is useful for obtaining regenerated silk fiber having excellent mechanical properties (Patent Document 1). Specifically, silk fiber originating from natural domesticated silkworm is first dissolved in an aqueous salt solution such as lithium bromide solution, followed by desalting through dialysis and cast-drying, to thereby yield a silk fibroin film, and this film is dissolved in HFIP.

Patent Document 1: Japanese Unexamined Patent Application Publication (Translation of PCT application) No. 7-503288

Also, since HFIP requires a prolonged time for completing dissolution, there has recently been reported use of hexafluoroacetone (HFA), which is a compound analogous to HFIP, to produce regenerated silk thread (Patent Document 2).

Patent Document 2: JP-A-2004-68161

However, since the objective of the development of those regenerated silk fibers was natural silk fiber, efforts had been exclusively directed to obtain such regenerated silk fiber that approximates the strength and elongation of natural silk fiber, and thus, no study has heretofore been performed regarding in vivo degrading ability of fiber.

Under the above circumstances, the present inventors have conducted studies on the in vivo degradation of regenerated silk fiber produced by use of a fluorine-containing solution, and have found that, in the presence of a poteolytic enzyme, the fiber is more easily degraded than natural silk fiber, and that when hexafluoroisopropanol is used as a spinning solution and hematin is added thereto, tensile strength of the resultant thread can be improved.

Incidentally, black sutures are favorably used by surgeons in United States of America, because they are easier to see against the background of body tissue. In recent years, also in Japan, use of back sutures has become more popular. However, since the dying steps in manufacture of black sutures are more intricate than white sutures, there exists demand for more convenient method to impart black color to sutures.

DISCLOSURE OF THE INVENTION

Problems to be Solved by the Invention

Accordingly, a first object of the present invention is to provide a spinning solution composition which is useful for producing regenerated silk fiber that exhibits strength and elongation approximating those of natural silk fiber, that quickly degrades in vivo, and that also can prevent inflammation by gradually releasing a drug.

A second object of the present invention is to provide a process for producing regenerated silk fiber that exhibits strength and elongation approximating that of natural silk fiber, that quickly degrades in vivo, and that optionally can prevent inflammation by means of sustained drug release.

A third object of the present invention is to provide regenerated silk fiber that exhibits strength and elongation approximating those of natural silk fiber, that quickly degrades in vivo, that optionally can prevent inflammation by means of sustained drug release, and that is suitable for surgical sutures.

Means for Solving the Problems

The above objects of the present invention have been attained by the provision of: a spinning solution composition containing silk fibroin and hematin in hexafluoroisopropanol which serves as a solvent; a process for producing regenerated silk fiber characterized by spinning the spinning solution composition in a coagulating bath; and regenerated silk fiber obtained through the production process.

Preferably, the above-mentioned silk fibroin which may be employed herein is obtained by first dissolving domesticated silkworm silk fiber that has undergone scouring in an aqueous salt solution, then removing the salt from the solution, and then removing water and drying (claim 2). Preferably, the silk fibroin content in the spinning solution composition falls within a range of 10 to 17 w/v % (claim 3). Preferably, the hematin content falls within a range of 0.03 to 0.15 parts by weight with respect to one part by weight of silk fibroin (claim 4). The spinning solution composition of the present invention can optionally contain an inflammation preventive drug so that an inflammation preventing function is imparted to the resultant regenerated silk fiber (claim 5).

The process for producing the regenerated silk material of the present invention is characterized by spinning the above-described spinning solution composition of the present invention in a coagulating bath (claim 6). Preferably, the solvent of the coagulating bath is methanol (claim 7), and the resultant regenerated silk fiber, after being dried, is preferably drawn to 2 to 4 times in length (claim 8).

According to the process of the present invention for producing the regenerated silk fiber, the spinning solution composition of the present invention may be spun and drawn in a coagulating bath (claim 9), and in this case, regenerated silk fiber can be provided with further elasticity (claim 12).

The regenerated silk fiber according to the present invention has a strength which compares favorably with that of natural silk fiber obtained through the process of the present invention (claim 10), and in particular, can be beneficially employed as a surgical suture material (claim 11).

Effects of the Invention

The regenerated silk fiber of the present invention produced from the spinning solution composition of the present invention exhibits both strength and elongation approximating those of natural silk fiber, as well as excellent biodegradability, and thus is useful as a material for producing suture threads, gauze, artificial blood vessels, etc.

BRIEF DESCRIPTION OF THE DRAWINGS

FIG. 1 shows solid-state NMR spectra, in which the Ala Cβ peak is focused on.

BEST MODE FOR CARRYING OUT THE INVENTION

Figure 1:
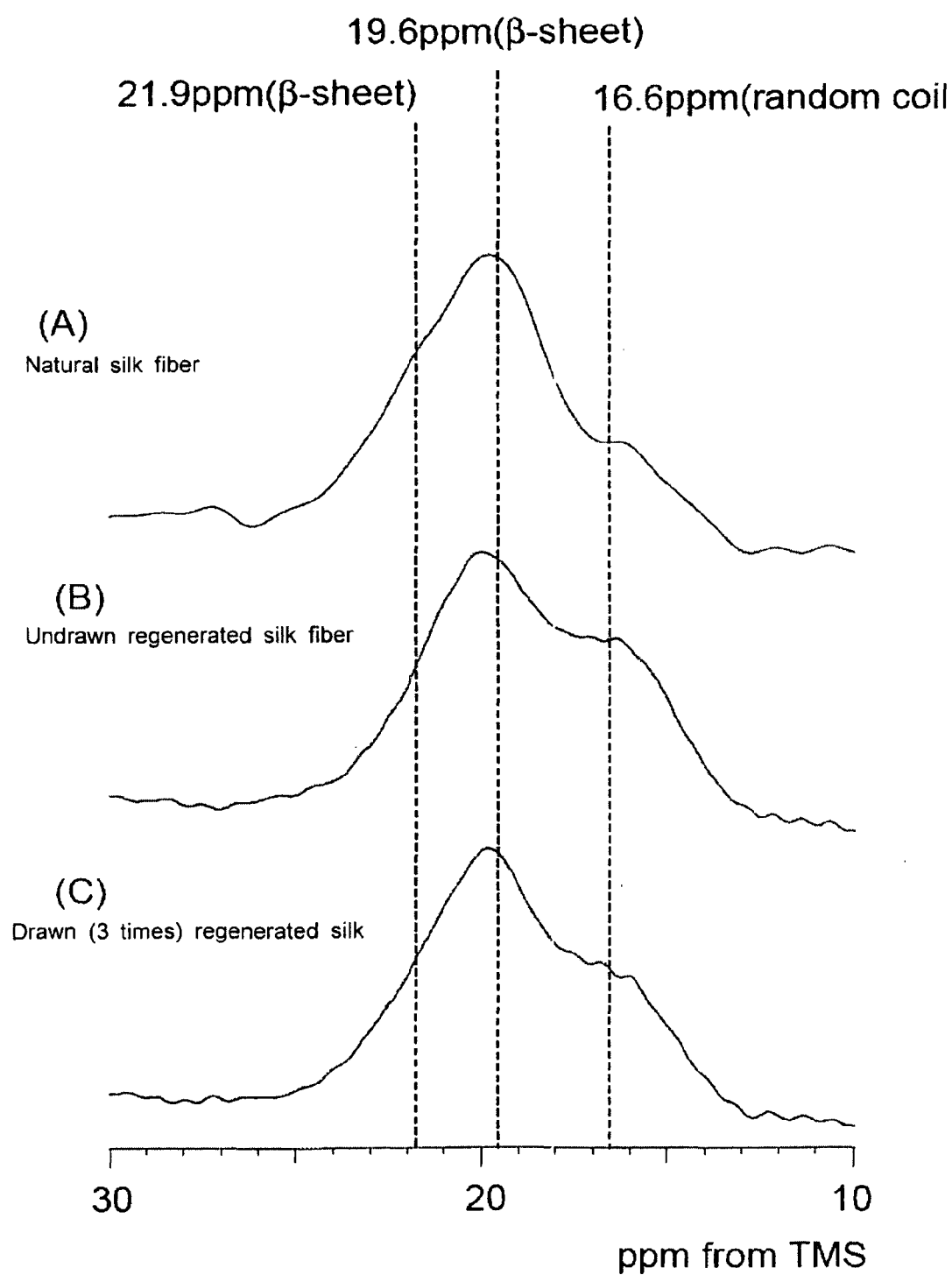

The spinning solution composition, the process for producing regenerated silk fiber, and the regenerated silk fiber, all falling within the scope of the present invention, will next be described in detail.

First, the spinning solution composition of the present invention is described. An inventive feature of the spinning solution composition of the present invention is that silk fibroin and hematin are contained in a hexafluoroisopropanol (HFIP) solvent.

No particular limitation is imposed on the process for producing the spinning solution composition of the present invention. However, since it is difficult to dissolve natural silk fibers such as domesticated silkworm silk fiber as is, in HFIP, an adequate known method is usually employed to obtain a solution; e.g., silk fibroin is first obtained by the steps of dissolving natural silk fiber in an aqueous salt solution, removing the salt, and removing water and drying, and the thus-obtained silk fibroin is dissolved in HFIP.

Specifically, cocoons were cut into pieces and scoured to obtain silk fibroin, and the obtained silk fibroin is dissolved in a salt solution such as lithium bromide solution, and then dialysis is performed to remove inorganic salts, whereby an aqueous silk fibroin solution is obtained. The thus-obtained aqueous solution is formed into silk fibroin film or is freeze-dried to provide spongy matter, and the material produced as such is dissolved in HFIP.

Alternatively, silk fiber waste may be directly dissolved in HFA, followed by removal of HFA to yield silk fibroin, and the thus-obtained silk fibroin may be dissolved in HFIP, without using the above-mentioned salt solution.

A specific example of the scouring method is given hereunder. For example, to 0.5 wt. % soap solution heated to 100° C., the above-mentioned cocoons are added, and the cocoons are subjected to reeling, followed by boiling for about 30 minutes while stirring. Thereafter, the cocoons are washed in distilled water heated to 100° C. This procedure is performed three times in total, after which the cocoons are again boiled for 30 minutes and washed, then dried to give silk fibroin which is free from protein coating silk fibroin (i.e., sericin) and other fats.

The above-described dissolution into a salt solution is performed by, for example, using an aqueous LiBr solution having a concentration of 40 to 80 wt. %. Silk fibroin is added to the bath of about 40° C., followed by shaking until no residue remains. At this point, the salt solution typically has a silk fibroin concentration of 5 to 40 wt. %.

The resultant aqueous silk fibroin/LiBr solution is subjected to filtration under reduced pressure by use of a glass filter or the like to remove dust and debris contained in the aqueous solution. Subsequently, using dialysis membrane made of cellulose or a similar material, dialysis is performed against distilled water, whereby salt-free aqueous silk fibroin solution is obtained.

When water is removed from the resultant aqueous solution, fibroin—the substance to be dissolved in HFIP—is isolated. Generally, the aqueous solution is spread on a plate and water is allowed to evaporate to thereby form a film, or, spray drying or a similar process is performed. Alternatively, through addition of distilled water, a diluted aqueous solution having a silk fibroin concentration of, for example, 2 w/v % or less may be prepared, followed by freeze-drying to give spongy silk fibroin.

The spinning solution composition of the present invention is prepared by adding the silk fibroin prepared as described above and hematin to a HFIP solvent. Typically, after the above-obtained silk fibroin is dissolved in a HFIP solvent, hematin is added to obtain a spinning solution composition.

The solution of silk fibroin in HFIP (hereinafter may be referred to as "silk fibroin/HFIP solution") is typically prepared by adding 10 to 17 w/v %, preferably 12 to 15 w/v % of silk fibroin to a HFIP solvent, stirring the resultant mixture to dissolve.

Hematin is a porphyrin compound represented by the formula below (iron(III) protoporphyrin). When it is added to be present in a spinning solution composition, black-dyed regenerated silk fiber can be easily obtained. Hematin has been approved by the FDA as a coloring dye for sutures, and enhances visibility of the sutures against the tissue of the living organism. In the present invention, commercially available products (for example, H3281 Hematin porcine by Sigma-Aldrich) may be expediently employed.

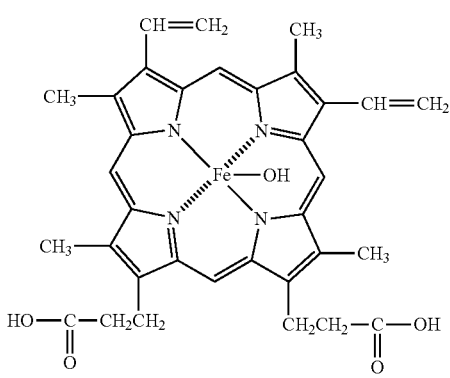

The spinning solution composition of the present invention is usually prepared by adding hematin (powder) to a silk fibroin/HFIP solution at a ratio of 0.03 to 0.15 parts by weight, preferably 0.05 to 0.10 parts by weight, based on 1 part by weight of silk, then stirring to disperse the powder in the solution. Since hematin (powder) may be degraded during storage, it is tightly sealed and stored in the dark.

The spinning solution composition of the present invention may contain an inflammation-preventing drug in an amount that would not impede the effect of the present invention. Thus, there can be obtained regenerated silk fiber which gradually releases a drug and can prevent inflammation. Examples of employable drugs include, but not limited to, triclosan, which has a bisphenol structure and exhibits antibacterial and antimycotic effects and tetracycline hydrochloride, which is typically used for the treatment of microbial infections.

Next, the process for producing the regenerated silk fiber of the present invention is described. According to the process for producing the regenerated silk fiber of the present invention, the above-described spinning solution composition of the present invention is employed as a starting spinning dope, and any of wet spinning, dry-jet spinning, dry spinning, and electrospinning may be performed. When long fiber is desired to be produced, wet spinning is preferred, in which silk fiber is spun into a coagulating bath through spinnerets, whereas when non-woven fabric is produced, electrospinning is preferred.

No particular limitation is imposed on the coagulating bath employed in the wet spinning method, so long as silk fibroin remains insoluble in the bath and HFIP can be dissolved therein. For example, water, methanol, ethanol, isopropyl alcohol, or acetone can be used. Among these materials, methanol is preferred for the reasons that it exhibits high fibroin coagulation, is safe to the environment, and is inexpensive.

In order to sufficiently remove HFIP, regenerated silk fiber is preferably left to stand still in the coagulating bath for several hours, and subsequently, air-drying is performed to give an undrawn sample. The undrawn sample is then subjected to drawing, through which strength comparable to that of natural silk fiber can be imparted. Preferably, drying is performed while tension is applied; application of tension can effectively prevent shrinkage and improve tensile characteristics of the regenerated silk fiber. Through drawing the regenerated silk fiber to 2 to 4 times in length, there can be obtained a drawn regenerated silk fiber of very uniform fiber thickness, having a diameter of about 20 micrometers to several hundred micrometers or thereabouts. Also, when cold drawing is performed after the fiber is taken out of the bath but while it is still wet, or the fiber is drawn in the coagulating bath, silk fiber of high elasticity can be obtained.

The draw ratio for the undrawn regenerated silk fiber is, as described above, 2.0 to 4.0 times, which ratios are generally attainable by drawing to provide regenerated silk fiber with a practical strength. The draw ratio of 4 times or more can attain a strength exceeding that of natural silk fiber. However, when continuous spinning is performed, a draw ratio of 2.0 to 3.0 is preferred. In this case, a draw ratio of 2 times or more can attain a breaking strength of 250 Mpa or more, which exceeds the breaking strength of regenerated fibers obtained from chitosan, cellulose, cow milk, peanuts, corn, soybeans, etc. ranging from 100 to 200 Mpa.

The thus-obtained regenerated silk fiber not only compares favorably with natural fiber in terms of both strength and elongation, but exhibits excellent in vivo degradability. Moreover, since the fiber allows arbitrary selection of fiber thickness and inclusion of pharmaceuticals, it is beneficially employed for producing surgical sutures, gauze, artificial blood vessels, among other materials. In particular, incorporation of hematin improves elongation of thread. Therefore, when silk monofilament having a diameter of 25 μm to 450 μm is used as a suture thread, inclusion of hematin provides the benefit of improved visibility, thus proving suitability of the regenerated silk fiber of the invention for surgical use (55th SPSJ (The Society of Polymer Science, Japan) Annual Meeting and 2006 Annual Meeting of The society of Fiber Science and Technology, Japan).

Also, since regenerated silk fiber containing hematin exhibits satisfactory durability in the color fastness test to sunlight (JIS L 0841-0843) and color fastness test to washing and laundering (JIS L 0844), nonwoven fabrics produced by electrospinning are advantageously employed as a gauze product.

The present invention will next be described in further detail by way of examples, which should not be construed as limiting the invention thereto.

Referential Example 1

Preparation of Domesticated Silkworm Silk Fibroin Samples

Cocoons (Shunrei×Shogetsu) of the 2004 autumn cocoon crop were cut into pieces (about 2 mm×10 mm or thereabouts) with scissors, and scoured through the standard method for removing protein (sericin), fat, and other substances that cover fibroin, to thereby obtain silk fibroin. Subsequently, the silk fibroin was dissolved in an aqueous LiBr solution (9 mol/L) so as to attain a concentration of 10 w/v %.

The aqueous solution was dialyzed against distilled water for 4 days using a cellulose dialysis membrane (Seamless Cellulose Tubing 36/32, product of Viskase Sales Corp.), whereby LiBr was removed. Subsequently, through centrifugation, dissolution residue, debris, and other waste were removed, to thereby obtain an aqueous solution of domesticated silkworm silk fibroin. Distilled water was added, and a diluted aqueous solution having a silk fibroin was prepared so that the solution concentration is adjusted to 2 w/v % or less. The resultant solution was frozen dried with liquid nitrogen, and freeze-dried for one day. Samples from which water was removed to a sufficient extent were stored under vacuum drying conditions. Freeze-dried silk fibroin samples were thus obtained.

Example 1

Each (1.2 g) of the freeze-dried silk fibroin samples obtained from Referential Example 1 was added to 10 mL of 1,1,1,3,3,3-hexafluoroisopropanol (produced by Wako Pure Chemical Industries, Ltd., hereafter referred to as HFIP), and dissolved with stirring for 2 days at room temperature. Subsequently, hematin (0.12 g; Hematin porcine by Sigma-Aldrich) was added thereto, to thereby obtain a spinning solution composition.

This spinning dope was added to a cylinder and, while jetting through a nozzle of 0.55 mm in diameter, spun in a coagulating bath of 100% methanol by use of a syringe pump, whereby regenerated silk fiber was obtained. The thus-spun thread was taken up with a motor, and left in the coagulating bath for 3 hours or more, followed by removal from the bath. Subsequently, the thread was unwound, and both ends of each thread sample were fixed and air-dried overnight. An undrawn sample was thus obtained.

Structural analysis of silk fibroin contained in the spinning dope was performed as follows. A silk fibroin/HFIP solution, whose silk fibroin concentration was adjusted to about 5 wt. %, was employed. Hematin was not contained in this solution. Solution $^{13}C$ NMR was performed (by use of an Alpha 500 NMR Spectrophotometer produced by JEOL; pulse delay: 2.5 sec; number of scans: 20,439 times; measured at 25° C.). The results of spectral analysis indicate that domesticated silkworm silk fibroin had undergone no degradation in the HFIP solution.

Moreover, when chemical shift values for AlaCβ—which serves as a good mirror that reflects correlation with structural details—and other major amino acids were compared with chemical shift values of silk fibroin in an aqueous solution system, peaks attributed to Cβ carbons of major amino acids were found to have shifted toward the high magnetic field side, and those attributed to Cα carbons were found to have shifted toward the low magnetic field side. From this finding, silk fibroin in an HFIP solution is inferred to contain a great number of helixes. Specifically, since AlaCβ chemical shift was observed at 14.6 ppm, which is on the high magnetic field side as compared with that at 15.8 ppm which is indicative of formation of a common α helix structure, it is considered that, in HFIP, a helix structure is frequently formed in the vicinity of AlaCβ of the domesticated silkworm silk fibroin molecule.

Also, using a JASCO J-805 spectrometer, circular dichroism spectrometry was performed at 25° C. on a silk fibroin/HFIP solution whose silk fibroin concentration had been adjusted to about 0.01 wt. %. The measurement suggested that, in HFIP, silk fibroin has a structure different from that of the typical helix structure.

Moreover, the ratio of the 222-nm value to the 205-nm value in a spectral diagram of domesticated silkworm silk fibroin in HFIP was found to be almost equal to the value shown by the $3_{10}$-helix structure reported by Toniolo, et al. (J. Am. Chem. Soc. 1996, 118, 2744-2745).

From the above findings, domesticated silkworm silk fibroin in HFIP is conjectured to have formed a $3_{10}$-helix structure. Therefore, the chemical shift, toward the lower magnetic field side as compared with the ordinary α helix, observed in solution NMR studies performed on the domesticated silkworm silk fibroin molecule, is considered to be attributed to the $3_{10}$-helix structure.

Next, the undrawn sample was attached to a sheet of coordinate paper by use of double-sided adhesive tape. The sample, together with the paper, was gripped by a fixed chuck and a movable chuck and drawn with a manually-operated uniaxial drawing machine (manufactured by Imoto Seisakusho). Thus, drawn regenerated silk threads having a diameter of about 20 µm to about several hundred µm were prepared. Each sample of the resultant regenerated silk threads was found to have a very uniform diameter which can never be achieved by natural fiber, and have a smooth surface. Also, the diameter of the silk threads was confirmed to vary depending on the viscosity of the spinning composition, spinning rate, spinneret nozzle diameter, take-up speed, draw ratio, etc.

In order to obtain information on local structure and secondary structure of the silk fibroin molecule of regenerated silk thread, solid-state $^{13}C$ CP/NMR analysis was performed. In this study, a CMX400 NMR spectrometer (produced by Chemagnetic) was used at room temperature. The measurement conditions are as follows.

[Measurement Conditions]
Pulse delay: 3.00 sec, Contact time: 1 msec, Scan: 12,000 times
[Measured Samples]
(A) Natural silk fiber
(B) Undrawn regenerated silk fiber
(C) Drawn (3 times) regenerated silk fiber FIG. 1 shows spectral profiles obtained from solid-state NMR spectrometry, in which the AlaCβ peak was focused on because the peak sensitively reflects structural details.

From FIG. 1 which shows the structural details of silk fibroin Ala, the tested samples were found to exhibit different intensity ratios. In drawn oriented samples, peak intensity attributed to random coil (at 16.6 ppm) tend to decrease, and β-sheet peak intensities (at 19.6 ppm and 21.9 ppm) tend to increase. The differences are considered to be resulted from more molecules being oriented along the fiber axis due to the effect of drawing.

Figure 2:
FIG. 2 shows wide-angle X-ray diffraction patterns obtained from undrawn regenerated silk fiber and drawn (3× in length) fiber, both according to the present invention.
Figure 2:

Also, wide-angle X-ray diffractometry was performed on undrawn regenerated silk thread and drawn (3 times) thread, using a rotating-target X-ray diffraction apparatus ULTRA18 manufactured by Rigaku Denki (50 kV, 250 mA, target: Cu) (FIG. 2). In this test, drawn samples showed diffraction spots, indicating improved orientation of the regenerated silk thread. FIGS. 2(A) and 2(B) show the wide-angle X-ray diffraction patterns of undrawn regenerated silk thread and drawn (3×) thread, respectively.

When X-ray scattering images of the HFIP drawn regenerated silk thread samples were compared with those of natural fiber originating from domesticated silkworm silk fibroin, the former exhibits lower orientation, but homology exists in diffraction spot pattern of the two groups. This result is attributed to the similarity of unit cells that constitute crystalline portions of the two groups. This indicates that, if fiber orientation can be further improved in drawn regenerated silk thread, a crystal structure could be formed that can compare favorably with natural fiber originating from domesticated silkworm silk fibroin in terms of fiber orientation.

Comparative Example 1

The procedure of Example 1 was repeated except that hexefluoroacetone hydrate (by SHIGMA) was used instead of HFIP, to thereby give a hematin-free spinning dope. Similar to Example 1, solution $^{13}C$ NMR analysis was performed. Also, through use of the obtained dope, undrawn samples were prepared. Wide-angle X-ray diffractometry was performed on undrawn regenerated silk thread and drawn (3 times) thread.

The chemical shift value as determined for AlaCβ of domesticated silkworm silk fibroin in HFA was 15.7 ppm. This value, which shifts towards the lower magnetic field side as compared with the value determined in HFIP, is in agreement with that of a typical α helix, and therefore, it is considered that, in HFA, domesticated silkworm silk fibroin is present in the α helix conformation. Thus, the solution structure presumably affects the molecular structure of fiber produced therefrom.

Through comparison with the data obtained from wide-angle X-ray diffractometry, it has been confirmed that the regenerated silk thread produced by use of HFIP solvent has better orientation than the regenerated silk fiber produced by use of HFA solvent.

<Scanning Electron Microscopy>

The obtained regenerated silk threads were observed under a scanning electron microscope for their diameter, surface structure, etc. In addition, non-woven silk-fibroin fabric produced through electrospinning was also analyzed for its fiber morphology. The measurement instrument employed was a Real Surface View Microscope VE-7800 (made by Keyence). Each sample was securely held with carbon tape, followed by measurement (deposition treatment was not performed). The accelerating voltage was 1.1 kV, working distance (WD) was 23 mm.

Example 2

Measurement of Elongation and Tensile Strength at Break

Next, the fiber samples were measured for elongation and tensile strength at break. The cross sectional area of fiber was calculated based on the fiber diameter obtained from observation under a scanning electron microscope. The measurement instrument employed was an EZ Graph (made by SHIMADZU; maximum tensile load of load cell: 5 N) and the test was performed at a speed of 10 mm/s. In order to prevent displacement of a sample, before measurement, a cardboard frame was prepared and a sample was affixed thereto with double-sided adhesive tape. A graph was created using averages of data measured at 10 points.

The results show a difference between regenerated silk thread produced through use of HFIP and regenerated silk thread produced through HFA in terms of fiber property. Regenerated silk thread produced by using HFIP ranked with silk fibroin, showing a similar level in terms of fiber strength, whereas regenerated silk thread produced by using HFA exhibited about ⅔ the strength. These results are considered to be attributed to difference in fiber orientation, which was observed in the analysis of X-ray scattering patterns. Also, in terms of fiber elasticity, both of the regenerated silk thread produced through use of HFA and that produced through use of HFIP exhibited about half the elasticity of natural fiber.

Figure 3:
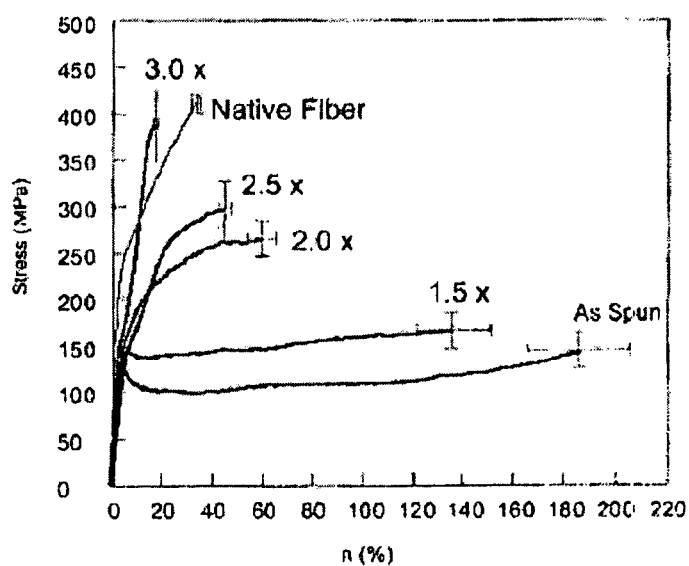
FIG. 3 is a chart showing changes in strength of silk fiber obtained at different draw ratios.

When draw ratio is varied, the resultant fiber gives a different strength. When measured in the as-spun state, regenerated silk thread produced from silk fibroin exhibits elongation of 2 times or more, showing very high elasticity. After undergoing draw treatment, the same thread exhibits as much an increase in strength. This is because drawing gives rise to orientation of silk fibroin molecules present in the fiber. FIG. 3 shows curves of variation in strength as determined on regenerated silk fiber samples having different draw ratios.

Moreover, stress at break was measured for drawn (4 times) HFIP regenerated silk fiber obtained through use of HFIP (hereinafter referred to simply as "HFIP regenerated silk fiber" and similar shortened expression is employed) and drawn (4 times) natural fiber originating from domesticated silkworm silk fibroin. Natural fiber originating from domesticated silkworm silk fibroin exhibited a stress at break of 400 MPa, and HFIP regenerated silk thread originating from domesticated silkworms exhibited a stress at break of 500 MPa. These results demonstrate that HFIP regenerated silk thread originating from domesticated silkworms can surpass domesticated silkworm silk fibroin natural fiber in terms of strength. The obtained mechanical property is comparable to that of the HFIP regenerated silk thread disclosed by Lock et al. (see WO93/15244).

Presumably, an increase in draw ratio resulted in an improved orientation in structure.

Example 3

Observation on Degradation

Figure 4:
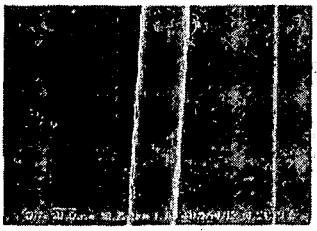
FIG. 4 shows electron microscopic photographs which show, in pairs for comparison, degradation of silk fiber by the action of a proteolytic enzyme.
Figure 4:
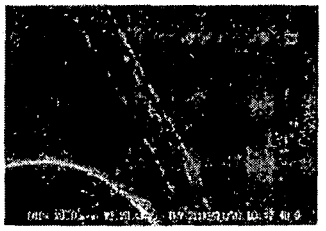
Figure 4:
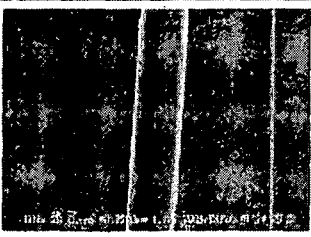
Figure 4:
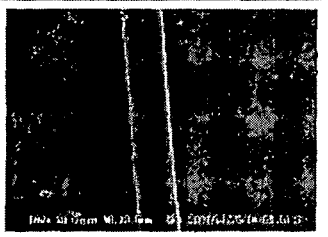
Figure 4:
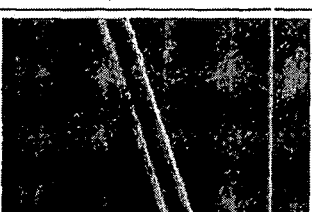
Figure 4:
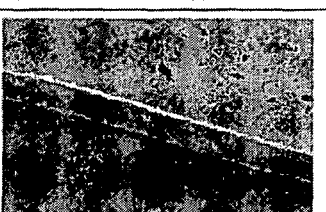
Figure 4:
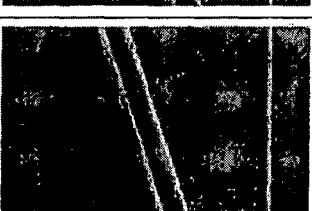
Figure 4:
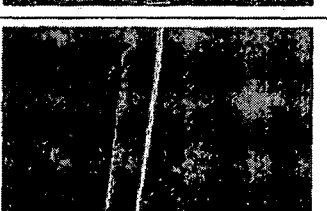

The drawn (3 times) thread and natural silk fiber samples prepared in Example 1 were immersed in a proteolytic enzyme solution. Sampling was performed on day 1, 3, 5, 7, and 9, whereby any time-course change appearing on the fiber surfaces was observed. The enzyme solution was prepared by dissolving one tablet of Dulbecco's phosphate buffered saline (PBS, product of Dainippon Pharmaceutical) in water (100 ml) and adjusting the concentration of enzyme (Protease produced by SIGMA) to 2.0 mg/ml. As a negative control, a PBS solution was employed. FIG. 4 shows some results of observation and comparison attained by using a scanning electron microscope.

The above-described observation has revealed that, in the case of natural silk fiber, on day 9, the fiber showed slight degradation caused by enzyme, and the fiber immersed in PBS showed no change on day 9 in terms of the surface structure of the fiber, as compared with day 1, maintaining the smoothness of as-spun fiber. Meanwhile, in the case of the drawn (3 times) thread of the present invention which was immersed in an enzyme solution, rough and unsmooth fiber surfaces were observed on day 9, clearly showing that enzymatic degradation had started. Also, no significant difference was observed between the two samples immersed in PBS solution.

INDUSTRIAL APPLICABILITY

The regenerated silk fiber according to the present invention overcomes problems involved in conventional silk sutures (braided sutures), and provides a number of advantages, including strength and elongation that approximates those of natural fiber, quick in vivo degradation, freely selectable fiber diameter, and ability to carry drugs. The regenerated silk fiber of the present invention finds utility in manufacture of such materials as sutures, gauze, and artificial blood vessels. Also, it is very likely that the fiber of the present invention can replace collagen, polylactic acid fiber, and other bioabsorbable materials. Therefore, regenerated silk fiber of the present invention has a great industrial applicability.

The invention claimed is:

1. A process for producing regenerated silk fiber, comprising spinning a spinning solution composition comprising hexafluoroisopropanol, which serves as a solvent, and contained therein, silk fibroin and hematin in a coagulating bath, drying the composition; and after drying, drawing the regenerated silk fiber to 2 to 4 times in length.

2. The process for producing regenerated silk fiber according to claim 1, wherein the solvent of the coagulating bath is methanol.

3. The process according to claim 1, wherein the silk fibroin is a silk fibroin which is obtained by first dissolving scoured domesticated silkworm silk fiber in an aqueous salt solution to thereby remove salt, and then removing water and drying.

4. The process according to claim 1, wherein the silk fibroin is present in the spinning solution composition in an amount of 10 to 17 w/v %.

5. The process according to claim 1, wherein the hematin is present in an amount of 0.03 to 0.15 parts by weight with respect to one part by weight of silk fibroin.

* * * * *

UNITED STATES PATENT AND TRADEMARK OFFICE
CERTIFICATE OF CORRECTION

PATENT NO. : 8,348,974 B2  
APPLICATION NO. : 12/307208  
DATED : January 8, 2013  
INVENTOR(S) : Tetsuo Asakura Page 1 of 1

It is certified that error appears in the above-identified patent and that said Letters Patent is hereby corrected as shown below:

On the title page, Item (86), the PCT information is incorrect. Item (86) should read:

--(86)  PCT No.:  PCT/JP2007/053929

& 371 (c)(1),
(2), (4) Date:  Dec. 31, 2008--

Signed and Sealed this
Nineteenth Day of March, 2013

Teresa Stanek Rea
*Acting Director of the United States Patent and Trademark Office*